United States Patent [19]

McRae

[11] Patent Number: Plant 6,207

[45] Date of Patent: Jun. 21, 1988

[54] HYBRID ASIATIC LILY NAMED STANDBY

[75] Inventor: Edward A. McRae, Boring, Oreg.

[73] Assignee: Melridge, Inc., Gresham, Oreg.

[21] Appl. No.: 861,919

[22] Filed: May 12, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant bearing large clusters of flowers particularly characterized by their rich pink color, their large size, their broad tepals, and their lack of any spotting. This combination is believed to be completely new in the upright Asiatic division of lilies suited to forcing and to mass commercial cultivation. The flowers are of excellent form and long persistence, both on the plant and as cut flowers, the plant is highly resistant to disease and shows high tolerance of virus, making this new lily an excellent garden plant. The clone is vigorous and is a good grower and propagator and its bulbs may be precooled and forced for out-of-season cut flower production.

1 Drawing Sheet

BACKGROUND OF THE INVENTION

This new variety of lily plant originated as a seedling selected from a group of seedlings planted by me at Sandy, Oreg., in the course of breeding efforts carried on by me with the object of producing spotless upright Asiatic lilies in a variety of pastel colors, well suited to forcing for cut flower production out-of-season, advantages heretofore unknown in the lily breeding art. To obtain the desired objective, I used as the seed parent the clonal cultivar 'Connecticut King' and as the pollen parent a clone selected from the 'Hallmark' strain and I selected two seedlings from the progeny of this first generation cross for intercrossing and the present plant was one of the seedlings produced in the second generation. The flowers of this seedling are characterized by large size, and upright orientation, lack of spots and a rich pink coloration, unique for this type of lily. This lead to my asexual reproduction of this new plant at Sandy, Oreg., by bulb scale propagation, and the clones appeared to possess to a high degree the desirable characteristics of hybrid vigor, great hardiness, and its blooms appeared to possess all of the desired characteristics of excellence of form, color, and habit, the large flowers being produced on a single stalk. Successive generations of this new plant produced by bulb scale propagation and by natural propagation from bulblets has demonstrated that the novel and distinctive characteristics of this new lily variety are fixed and hold true under asexual propagation from generation to generation.

As observed at Sandy, Oreg., this new lily appears to be well suited to forcing out-of-season when the bulbs are dug at the appropriate time and properly precooled. For example, October-dug bulbs properly precooled and potted in January will flower in an average of 80 to 85 days, under glass in western Oregon, with no supplementary lighting and at moderate greenhouse temperatures.

DESCRIPTION OF THE DRAWING

My new variety of lily plant is illustrated by the accompanying photographic drawing, which shows a face view of an open bloom in full color and illustrates the flower form, the tepal arrangement, and, in particular, the distinctive large and unspotted pink flowers.

DESCRIPTION OF THE NEW VARIETY

The following is a detailed description of my new variety of Asiatic hybrid lily with nomenclature according to The International Lily Register of The Royal Horticultural Society of London (Second Edition, 1969) and with color designations according to The R.H.S. Colour Chart published by The Royal Horticultural Society in 1966.

THE PLANT

Origin: Seedling.

Parentage:

*Seed parent.*—A selected seedling from a cross of Lilium 'Connecticut King' and a selected clone from the Lilium 'Hallmark' strain.

*Pollen parent.*—A different selected seedling from the cross of 'Connecticut King' and a selected clone from the Lilium 'Hallmark' strain.

Classification:

*Horticultural.*—Division I-A, Upright Hybrid Asiatic Lilies, according to The Horticultural Classification of Lilies by The Royal Horticultural Society of London, England.

*Commercial.*—Hybrid Lilium Clone.

Form: An erect and stately single stem.

Height: About 100 to 110 cm. from bulbs of about 15 to 18 cm. in circumference, provided their light levels are adequate; low levels may cause "stretching".

Growth: Vigorous and upright.

Foliage:

*Quantity.*—Abundant.

*Leaf size.*—About 8 to 10 cm. long and about 0.7 to 1.0 cm. wide.

*Leaf shape.*—Lanceolate with acuminate tip.

*Texture.*—Leathery.

*Aspect.*—Glossy.

*Color.*—Dark green, but lighter on the lower side.

Bulbs:

*Size.*—Varying according to age and ranging up to 25 cm. in circumference for commercial use.

*Color.*—White.

THE BUD

Form: Long ovoid with obtuse tip.

Size: About 8 to 9 cm. long and about 5 cm. in circumference just prior to opening.

Opening rate: The bud opens slowly, and generally takes about one hour in response to morning light.

Color: Rich pink underlying soft green just prior to opening and as the tepals begin to unfurl.

Peduncle:

*Length.*—About 4 to 6 cam. in average, but may elongate if light levels are too low or if the bulbs have been improperly stored prior to forcing.

*Color.*—Dark green with a plum overlay.

THE FLOWER

Blooming habit: Annually, once and profusely in mid-season for Asiatic lilies.

Size: Large, about 16 to 19 cm. in diameter, the outer tepals being about 2 to 2.5 cm. wide and the inner tepals being about 3 cm. wide.

Borne: In a signal racemic form having from 9 to 11 buds (from a bulb about 18 cm. in circumference).

Shape: Cup-shaped when first opening and becoming flattened as the tepals recurve by the second day.

Tepalage:

*Number.*—Six.

*Arrangement.*—Hexagonal with both inner and outer tepals spaced apart.

*Appearance.*—Shiny.

*Color.*—The flowers are distinguished by their rich pink color pattern, in which the base of the tepals is red, 47C-D, shading into 48C-D at the tepal tips and margins. The tepal midrib is of a deeper pink tone, 47C-D, extending from the nectaries to about 2 cm. from the tepal tip. The color may decrease slightly in intensity under conditions of low light or unusually high temperatures.

*Spotting.*—The tepals are entirely unspotted.

*Longevity.*—The tepals stay on the stems about three weeks.

*Color changes.*—The flowers become slightly lighter and "bluer" as they age becoming 57D to 58D. Low light levels and extreme heat may cause the pink pigmentation to decrease in intensity.

Pedicel:

*Length.*—About 6 to 10 cm., in average.

*Form.*—Sturdy and ascending up to 45° from the horizontal. Secondary buds very rarely occur.

*Color.*—Dark green with plum overlay.

Disease resistance: The flower and the plant are resistant to disease, and in particular being resistant to Fusarium Bulb Rot and Botrytis Blight.

Fragrance: None.

Lasting quality: The flower is long lasting, both on the plant and as a cut flower.

REPRODUCTIVE ORGANS

Stamens:

*Number.*—Six.

*Arrangement.*—Typical of genus Lilium.

Pollen and anthers (Dehisced): Greyed orange, 171A.

Filaments:

*Length.*—About 5 cm.

*Color.*—Soft pink, 62D.

Pistil:

*Number.*—One.

Style: About 5 cm. long.

Stigma: Soft green with light plum overlay.

The ovary: The ovaries are characteristic of genus Lilium.

THE FRUIT

Fertility: The fruit is fertile.

Shape: Ovoid.

Color at maturity: Soft brown, sometimes overlaid with soft plum.

This new variety of Asiatic lily most nearly resembles the variety 'Zephyr' (Pat. Pending) but has larger flowers with no spotting, broader tepals, and a much deeper pink color. The new variety has stronger stems than does 'Zephyr' when forced into flower out-of-season.

I claim:

1. A new and distinctive variety of Asiatic hybrid lily, substantially as herein shown and described, characterized by its large, broad tepalled flowers of rich pink coloration which are completely unspotted; by the excellence of its flower form, its high resistance to disease and tolerance of virus; its vigorous growth habit and rapid natural propagation; and its versatility both as a garden plant and as a cut flower producer from precooled bulbs forced under glass out-of-season.

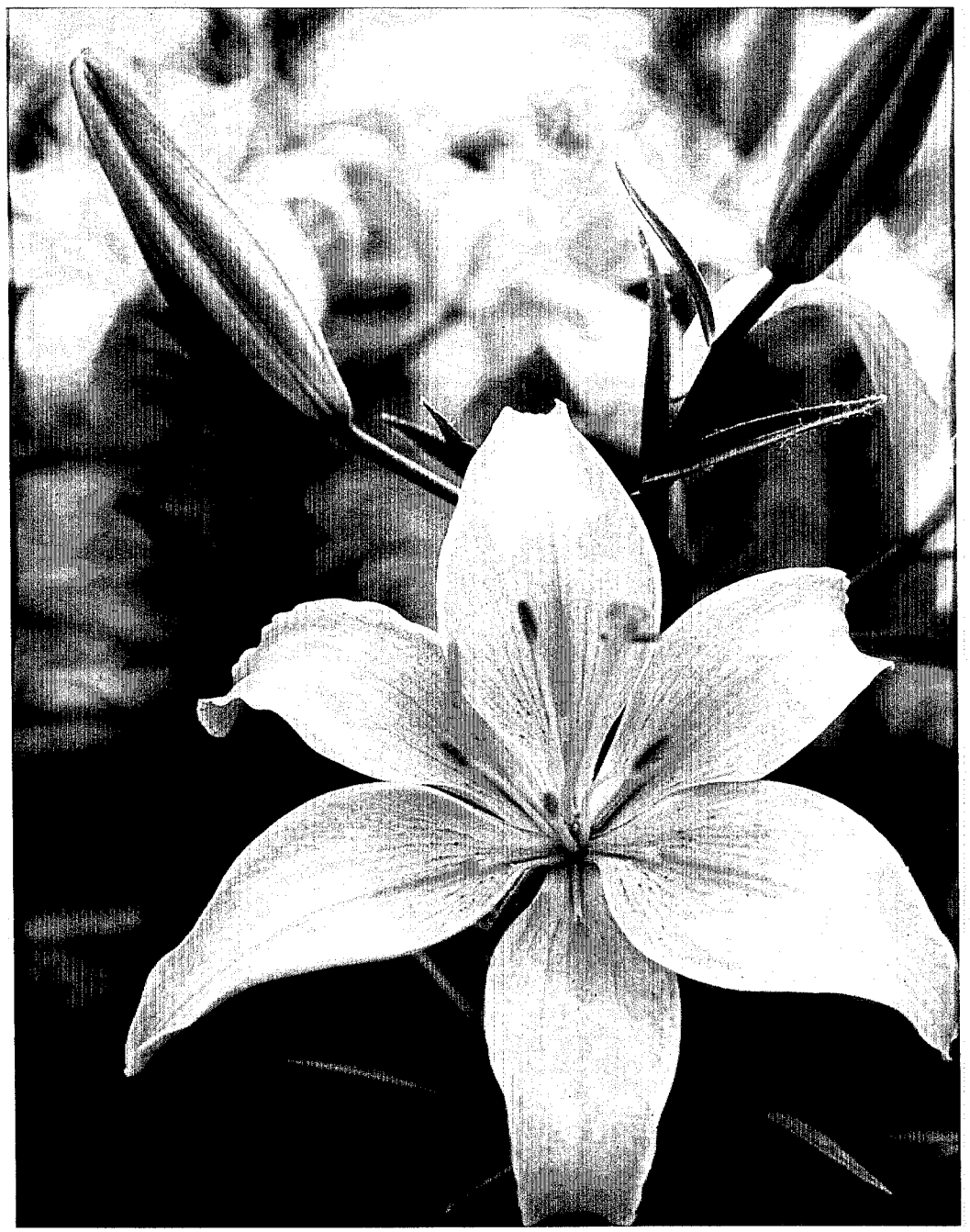

* * * * *